US010411510B2

(12) United States Patent
Sherman et al.

(10) Patent No.: US 10,411,510 B2
(45) Date of Patent: Sep. 10, 2019

(54) INDUCTIVELY-POWERED SURGICAL INSTRUMENT SYSTEM AND METHOD

(71) Applicant: DePuy Synthes Products, Inc., Raynham, MA (US)

(72) Inventors: Jason T. Sherman, Warsaw, IN (US); Sherrod A. Woods, Fort Wayne, IN (US); Matthew R. Dressler, Fort Wayne, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 15/814,145

(22) Filed: Nov. 15, 2017

(65) Prior Publication Data

US 2018/0076665 A1      Mar. 15, 2018

Related U.S. Application Data

(63) Continuation of application No. 14/515,771, filed on Oct. 16, 2014, now Pat. No. 9,837,862.

(51) Int. Cl.
| | |
|---|---|
| *H01F 38/14* | (2006.01) |
| *H02J 50/10* | (2016.01) |
| *H02J 7/02* | (2016.01) |
| *A61B 50/00* | (2016.01) |
| *A61L 2/28* | (2006.01) |
| *A61B 50/33* | (2016.01) |
| *A61B 50/34* | (2016.01) |
| *H02J 7/00* | (2006.01) |
| *A61B 17/00* | (2006.01) |
| *A61B 50/30* | (2016.01) |
| *A61L 2/04* | (2006.01) |

(52) U.S. Cl.
CPC .............. *H02J 50/10* (2016.02); *A61B 50/00* (2016.02); *A61B 50/33* (2016.02); *A61B 50/34* (2016.02); *A61L 2/28* (2013.01); *H02J 7/025* (2013.01); *A61B 2017/00411* (2013.01); *A61B 2050/005* (2016.02); *A61B 2050/006* (2016.02); *A61B 2050/008* (2016.02); *A61B 2050/0083* (2016.02); *A61B 2050/3008* (2016.02); *A61L 2/04* (2013.01); *A61L 2202/24* (2013.01); *H02J 7/0042* (2013.01)

(58) Field of Classification Search
CPC .......... H02J 7/0042; H02J 50/10; H02J 7/025; A61L 2202/24; A61L 2/28; A61L 2/04; A61B 2017/00411; A61B 50/00; A61B 2050/005; A61B 2050/006; A61B 2050/008; A61B 2050/0083; A61B 50/33; A61B 50/34; A61B 2050/3008
See application file for complete search history.

(56) References Cited

U.S. PATENT DOCUMENTS

| | | |
|---|---|---|
| 8,482,160 B2 | 7/2013 | Johnson et al. |
| 9,124,308 B2 | 9/2015 | Metcalf |
| 9,837,862 B2 | 12/2017 | Sherman et al. |

(Continued)

*Primary Examiner* — Alfonso Perez Borroto
*Assistant Examiner* — Esayas G Yeshaw
(74) *Attorney, Agent, or Firm* — Barnes & Thornburg LLP

(57) ABSTRACT

A surgical instrument system and method are disclosed. The surgical instrument system includes an instrument case and a charging plate that may be placed in a sterile surgical field. The charging plate is configured to receive electrical power from outside the sterile surgical field and transmit that electrical power to other devices within the sterile field.

19 Claims, 10 Drawing Sheets

(56) References Cited

U.S. PATENT DOCUMENTS

| | | |
|---|---|---|
| 2007/0236174 A1 | 10/2007 | Kaye |
| 2009/0096413 A1 | 4/2009 | Partovi et al. |
| 2009/0153060 A1* | 6/2009 | Shun'ko ............... H01J 37/321 315/111.21 |
| 2010/0108761 A1* | 5/2010 | Nycz .................... G06Q 10/087 235/385 |
| 2012/0071778 A1* | 3/2012 | Wang .................... A61B 5/0002 600/539 |
| 2012/0161530 A1 | 6/2012 | Urano |
| 2013/0127406 A1* | 5/2013 | Winger .................. H02J 7/025 320/108 |
| 2013/0264997 A1 | 10/2013 | Lee et al. |
| 2014/0091758 A1 | 4/2014 | Hidaka et al. |
| 2014/0368163 A1 | 12/2014 | Ho |
| 2015/0181631 A1* | 6/2015 | Lee ....................... H04W 76/10 455/41.2 |
| 2015/0326061 A1 | 11/2015 | Davison et al. |
| 2015/0362333 A1 | 12/2015 | Miller et al. |
| 2016/0072338 A1 | 3/2016 | Makwinski et al. |
| 2016/0094078 A1 | 3/2016 | Graham et al. |
| 2016/0181875 A1 | 6/2016 | Long et al. |

* cited by examiner

INDUCTIVELY-POWERED SURGICAL INSTRUMENT SYSTEM AND METHOD

This application claims priority to U.S. patent application Ser. No. 14/515,771, which was filed on Oct. 16, 2014 and is expressly incorporated herein by reference.

TECHNICAL FIELD

The present disclosure relates generally to systems used to manage instruments used during a surgical procedure, more specifically, to instrument cases used to charge surgical instruments remotely during surgery.

BACKGROUND

Reusable surgical instruments must be sterilized between uses. Generally, surgical instruments used in surgery are autoclaved before use in a subsequent surgery. The process of autoclaving involves high pressures and high heat. The autoclaving process prevents reusable surgical items from being made of certain types of materials, including many plastics. Generally, reusable surgical instruments are made of metal so that they can withstand the autoclaving process.

Many surgical procedures utilize surgical instruments that include one or more electrically-powered components. Some of these surgical instruments may be powered by electrical cables connected to wall outlets, while other surgical instruments may include rechargeable batteries.

SUMMARY

According to one aspect, a metallic surgical instrument case includes a bottom wall and number of side walls extending upwardly from the bottom wall to define a chamber sized to receive surgical instruments. A lower housing is secured underneath the instrument case. The lower housing includes a first induction coil and related circuitry to receive power from a primary induction coil located outside the sterile area. An upper housing is positioned within the chamber of the metallic instrument case. The upper housing includes second induction coil that is electrically connected to the first induction coil so that the second induction coil can receive power from the first induction coil.

BRIEF DESCRIPTION OF THE DRAWINGS

The detailed description particularly refers to the following figures, in which.

DETAILED DESCRIPTION OF THE DRAWINGS

Figure 1:
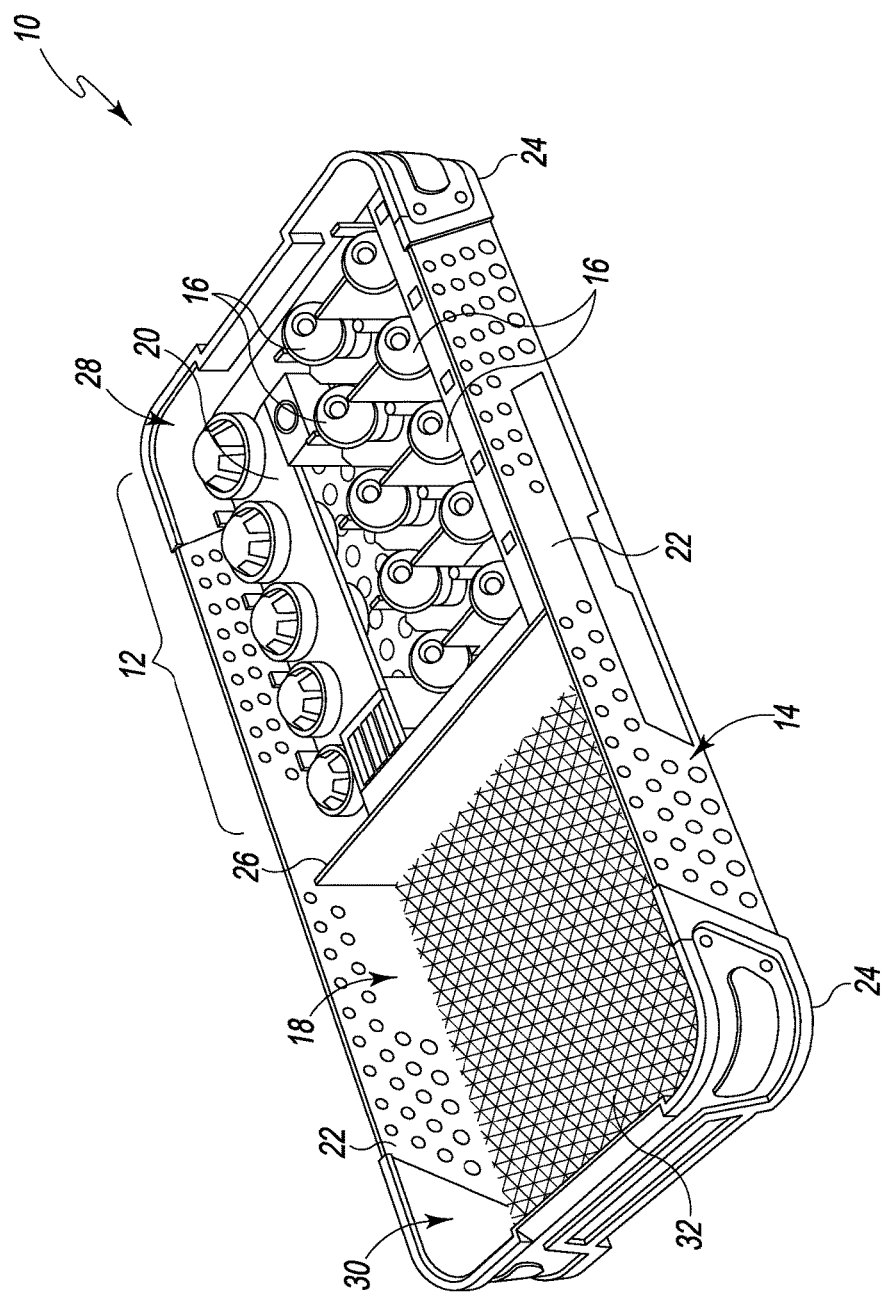
FIG. 1 is a perspective view of a surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, there is shown a surgical instrument system 10. The system 10 includes a plurality of surgical instruments 12 that are contained within a surgical crate or case 14. The surgical instruments 12 include a number of electrically-powered surgical instruments 16 that may require electrical power during use. The instruments 16 may include so-called "smart surgical instruments" that may include circuitry that assists and/or guides the user of the surgical instrument, provides information to a user about a patient or surgical procedure, and/or communicates with other devices during the surgical procedure. As described in greater detail below, the case 14 includes a charging plate 40 that is configured to receive power from outside of a sterilized surgical field and provide power to the instruments 16 in the sterilized surgical field.

In other embodiments, the case 14 may also house one or more prosthetic components that are configured to be implanted in a patient's body. The prosthetic components may also include electrically-powered devices that may require electrical power during use. It should be appreciated that the surgical instruments and prosthetic components may also include other surgical instruments or prosthetic components that do not require electrical power.

As shown in FIG. 1, the case 14 includes a chamber 18 that is sized to house the surgical instruments 12. The chamber 18 is defined by a bottom wall 20 and a number of side walls 22 extending upwardly from the bottom wall 20. The case 14 also includes a number of feet 24, which engage an instrument table or holding surface. In the illustrative embodiment, the case 14 is assembled from a number of components that are formed from metallic materials such as, for example, stainless steel. As a result, the case 14 may be sterilized between surgical procedures. In other embodiments, the case 14 may be formed from other materials that may be autoclaved or otherwise sterilized, including, for example, cobalt chromium, aluminum, or other suitable metallic material.

The case 14 illustratively includes an inner wall 26 that divides the chamber 18 into two sub-chambers 28, 30. The sub-chamber 28 defines a storage area for the surgical instruments 12, while the sub-chamber 30 defines a work area in which the instruments 12 may be placed during a surgical procedure. As shown in FIG. 1, a nipple mat 32 is positioned in the sub-chamber 30 and is adapted to receive surgical instruments during surgery.

Figure 2:
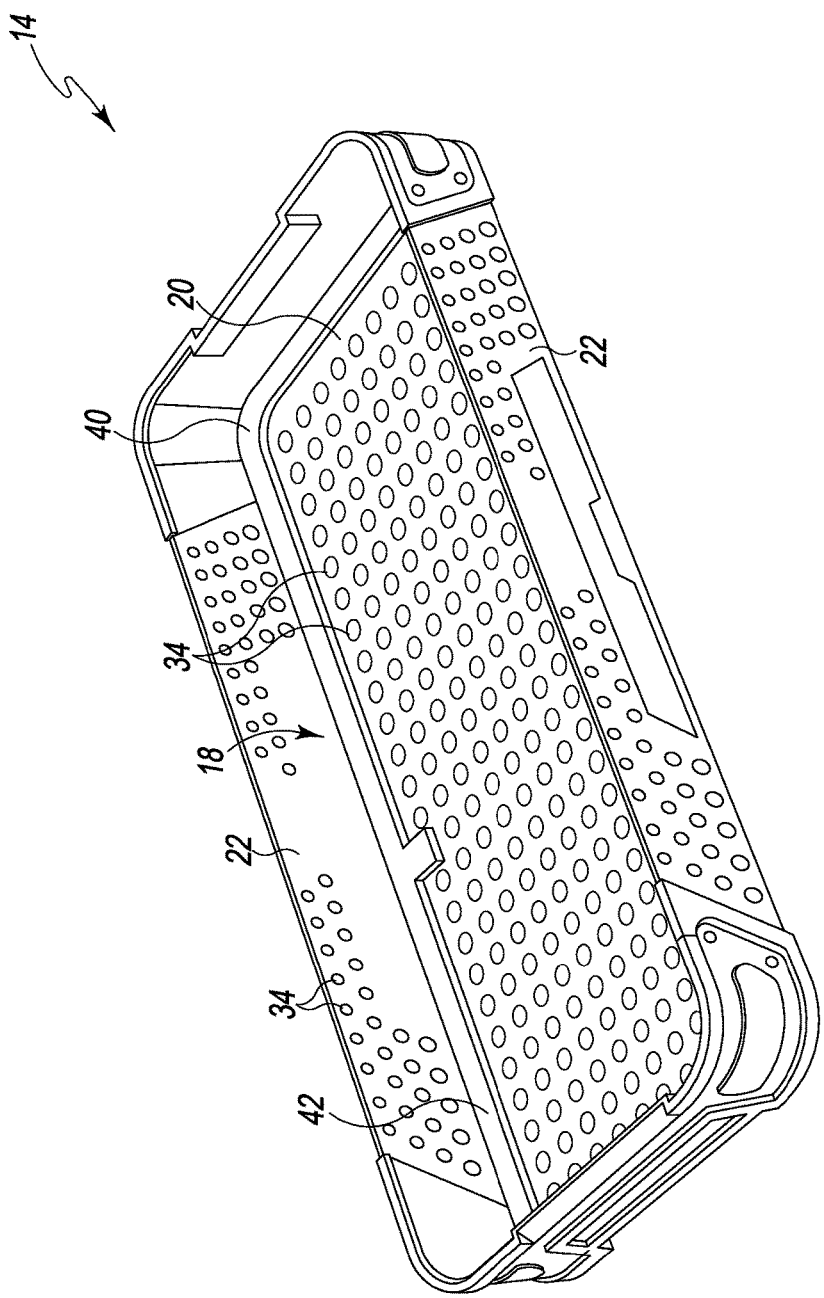
FIG. 2 is a perspective view of a surgical instrument case of the surgical instrument system of FIG. 1.

Referring now to FIG. 2, the case 14 is shown with the nipple mat 32, the instruments 12, and the inner wall 26 removed. A plurality of openings or through-holes 34 are defined in the walls 20, 22 of the case 14. As described above, the case 14 includes a charging plate 40 that is configured to receive inductive power from outside of a sterilized surgical field and provide inductive power to the instruments 16 in the sterilized surgical field. The charging plate 40 includes an upper housing 42 that is positioned in the chamber 18 and a lower housing 44 (see FIG. 3) that is positioned below the chamber 18. The housings 42, 44 are formed from non-conductive materials such as, for example, radel, celcon, polyether ether ketone (PEEK), or silicone.

The upper housing 42 of the charging plate 40 is shaped to match the outer dimensions of the chamber 18 of the case 14. In other embodiments, the housing 42 may be sized to be positioned only within, for example, the working area subchamber 30. While the housing 42 has a substantially rectangular shape, it should be appreciated that in other embodiments the upper housing 42 may be circular, oval, or other geometric shape. In the illustrative embodiment, the upper housing 42 is connected to the lower housing 44 through the bottom wall 20 of the case via a connector assembly 50, which is shown in FIG. 3.

Figure 3:
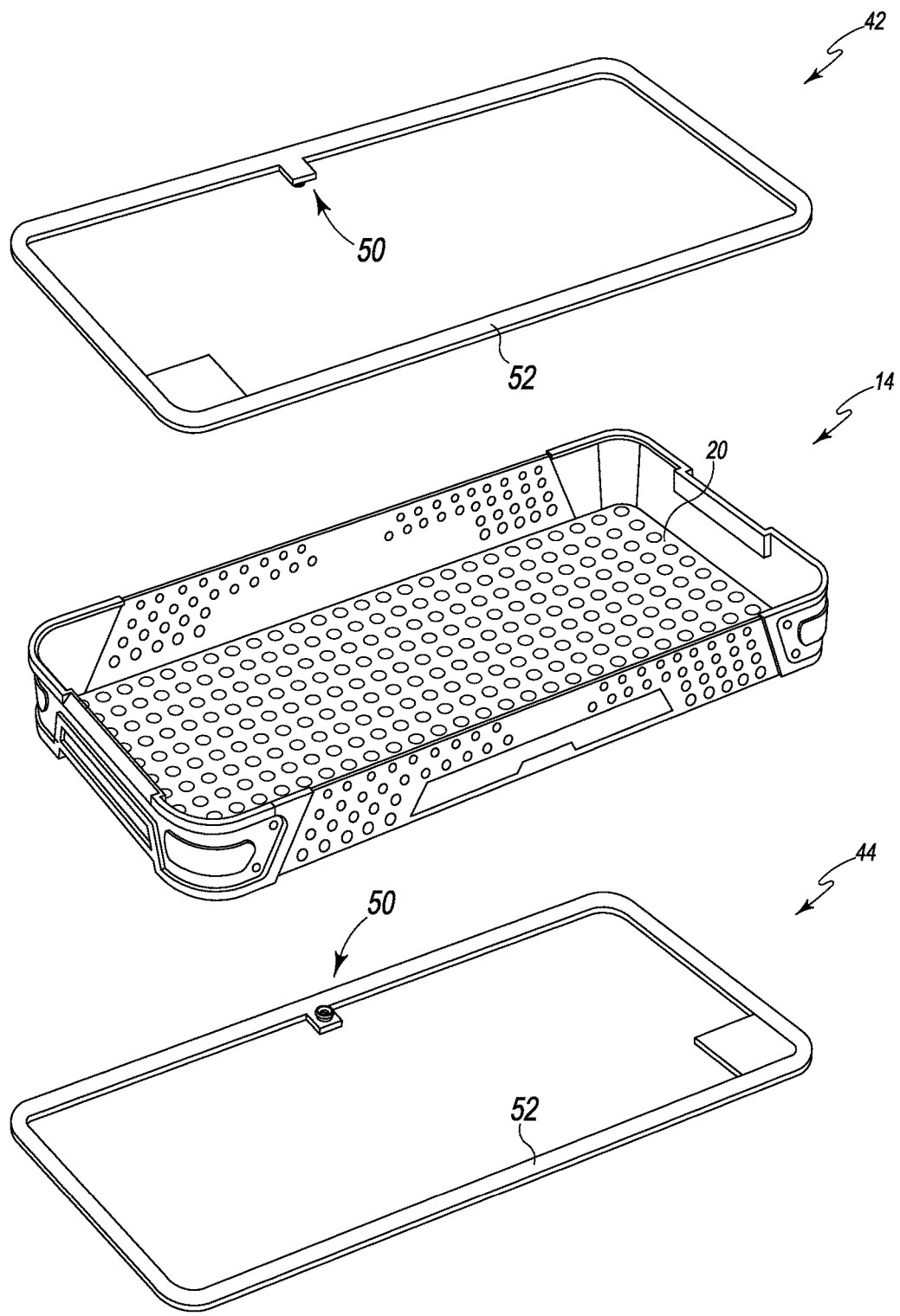
FIG. 3 is a an exploded diagram of the surgical instrument case of FIG. 2.

As shown in FIG. 3, the lower housing 44 of the charging plate 40 is shaped to match the dimensions of the upper housing 42. As such, the housing 44 has a substantially rectangular shape. It should be appreciated that in other embodiments the lower housing 44 may be circular, oval, or other geometric shape that matches the shape of the upper housing 42.

Figure 4:
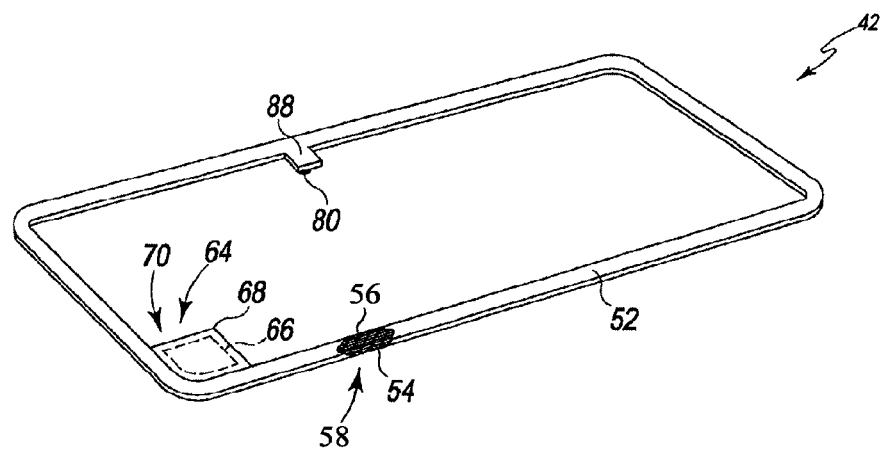
FIG. 4 is a perspective view of an upper housing of a charging plate of the surgical instrument case of FIG. 2.
Figure 5:
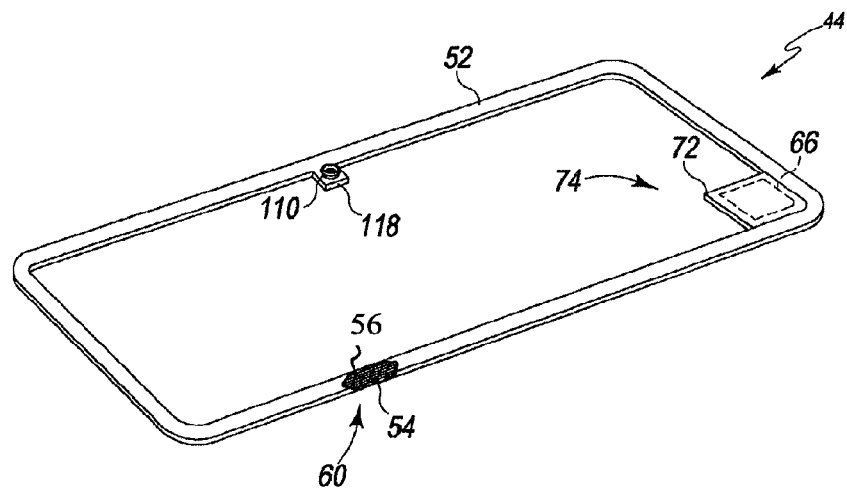
FIG. 5 is a perspective view of a lower housing of a charging plate of the surgical instrument case of FIG. 2.

Each of the housings 42, 44 include a tubular frame 52 that defines the rectangular shape. As shown in FIGS. 4-5, a hollow passageway 54 is defined in each of the frames 52, and the charging plate 40 includes an electrical coil 56 that is positioned in each passageway 54. Each coil 56 is formed from strands of conductive wire such as, for example, copper wire, that have been formed into a rectangular shape. It should be appreciated that in other embodiments the coils may have different configurations.

In the illustrative embodiment, the coil 56 in the upper housing 42 is a primary coil 58 that generates an alternating magnetic field, and the coil 56 in the lower housing 44 is a secondary coil 60. As described in greater detail below, the secondary coil 60 may be inductively coupled with a charging station 62 that induces an electrical current in the secondary coil 60 to transfer energy in the primary coil 58. That energy may then be transferred to the primary coil 58 via the connector assembly 50 for transmission to the surgical instruments 16. In the illustrative embodiment, each of the coils 56 defines a loop, which provides more efficient power transfer.

As shown in FIGS. 4-5, each of the housings 42, 44 also includes a casing 64 that is secured to the tubular frame 52. Each casing 64 houses electrical circuitry 66 that is connected to each coil 56. As described in greater detail below, the circuitry 66 is configured to improve the coupling between induction coils 56 and thereby increase the efficiency of the power transfer to the secondary coil 60 and the power transfer from the primary coil 58. As shown in FIGS. 4-5, the casing 68 of the upper housing 42 is positioned at an inner corner 70 of the upper housing 42, while the casing 72 of the lower housing 44 is positioned at an opposite, inner corner 74 of the lower housing 44.

As described above, the upper housing 42 is connected to the lower housing 44 via a connector assembly 50. In the illustrative embodiment, the connector assembly 50 is also configured to secure each of the housings 42, 44 (and hence charging plate 40) to the case 14. The connector assembly 50 includes a connector 80 that extends from a connector support 88 attached to the tubular frame 52 of the upper housing 42. The connector 80 is configured to engage a connector 110 that extends from a connector support 118 attached to the frame 52 of the lower housing 44. The connector 110 of the lower housing 44 is configured to engage the bottom wall 20 of the case 14, as described in greater detail below.

Figure 6:
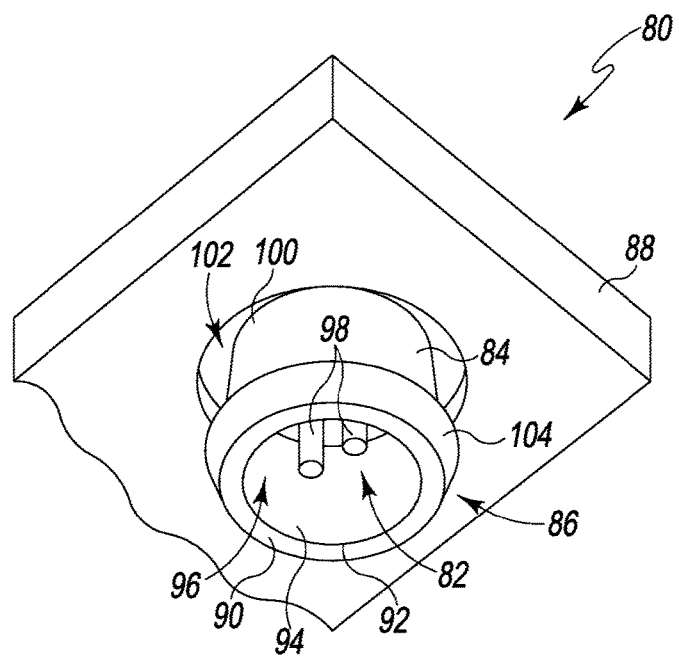
FIG. 6 is a perspective view of a connector of the upper housing of FIG. 4.

As shown in FIG. 6, the connector 80 of the upper housing 42 includes a plug 82, a connector body 84 that surrounds the plug 82, and a fastening mechanism 86 that interfaces with the connector 110 of the lower housing 44. The connector body 84 is formed from a non-conductive material such as, for example, a deformable plastic. The connector body 84 is tubular in shape and extends outwardly from the connector support 88 to a distal end 90. An opening 92 is defined in the distal end 90 and an inner wall 94 extends inwardly from the opening 92 to define an aperture 96. As shown in FIG. 6, the plug 82, which includes two prongs 98, is positioned in the aperture 126. Each of the prongs 98 is formed from a conductive material such as, for example, copper, and is electrically connected to the primary coil 58 of the upper housing 42. As described in greater detail below, the prongs 98 are sized to be received in a socket 112 of the lower housing connector 110, and the aperture 96 is sized to receive the socket 112 when the connector assembly 50 is assembled.

The connector body 84 includes a proximal end 100 that is positioned in a recess 102 defined in the connector support 88. As described above, the connector 80 also includes a fastening mechanism 86 that interfaces with the connector 110 of the lower housing 44. In the illustrative embodiment, the fastening mechanism 86 includes an annular flange 104 that extends outwardly from the distal end 90 of the connector body 84. The annular flange 104 is configured to engage the connector 110 to secure the connectors 80, 110 together. It should be appreciated that in other embodiments the fastening mechanism may include other arrangements of tabs, pins, adhesives, and so forth to secure the connector 80 to the connector 110.

Figure 7:
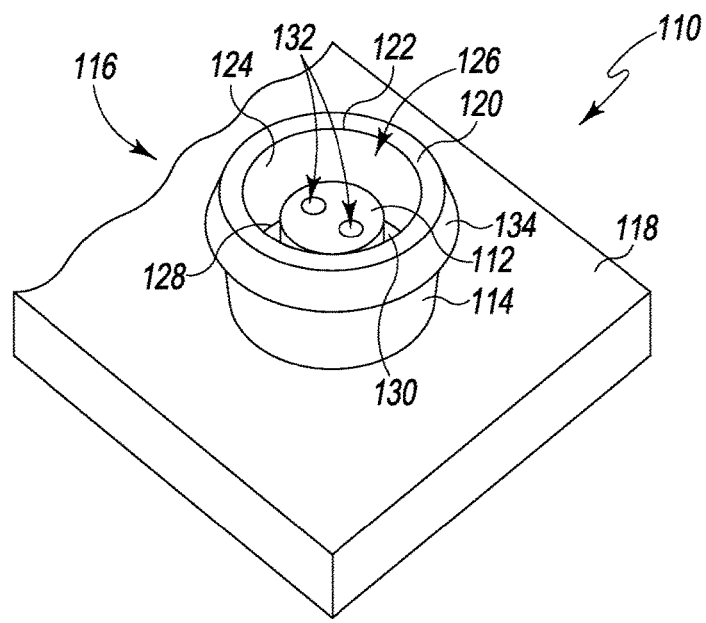
FIG. 7 is a perspective of a connector of the lower housing of FIG. 5.

As shown in FIG. 7, the connector 110 of the lower housing 44 includes a socket 112, a connector body 114 that surrounds the socket 112, and a fastening mechanism 116 that interfaces with the bottom wall 20 of the instrument case 14. The connector body 114 is formed from a non-conductive material such as, for example, a deformable plastic. Similar to the connector body 84 of the upper housing 42, the connector body 114 is tubular in shape and extends outwardly from the connector support 118 to a distal end 120. An opening 122 is defined in the distal end 120 and an inner wall 124 extends inwardly from the opening 122 to define an aperture 126. As shown in FIG. 7, the connector body 114 further includes an annular groove 128 that is defined at the base 130 of the aperture 126.

The socket 112, which includes a pair of receptacles 132, is positioned in the aperture 126. Each receptacle 132 is lined with a conductive material such as, for example, copper, and is electrically connected to the secondary coil 60 of the lower housing 44. Each receptacle 132 is sized to receive a corresponding prong 98 of the upper housing connector 80 such that the secondary coil 60 may be connected with the primary coil 58 when the connector assembly 50 is assembled. It should be appreciated that in other embodiments the connector assembly 50 may include additional prongs and receptacles according to the nature of the electrical circuit.

As described above, the connector 110 includes a fastening mechanism 116 that interfaces with the bottom wall 20 of the instrument case 14. In the illustrative embodiment, the fastening mechanism 116 includes an annular flange 134 that extends outwardly from the distal end 120 of the connector body 114. As described in greater detail below, the annular flange 134 engages the bottom wall 20 of the instrument case 14 to secure the connector 110 (and hence the lower housing 44) to the instrument case 14.

Figure 8A:
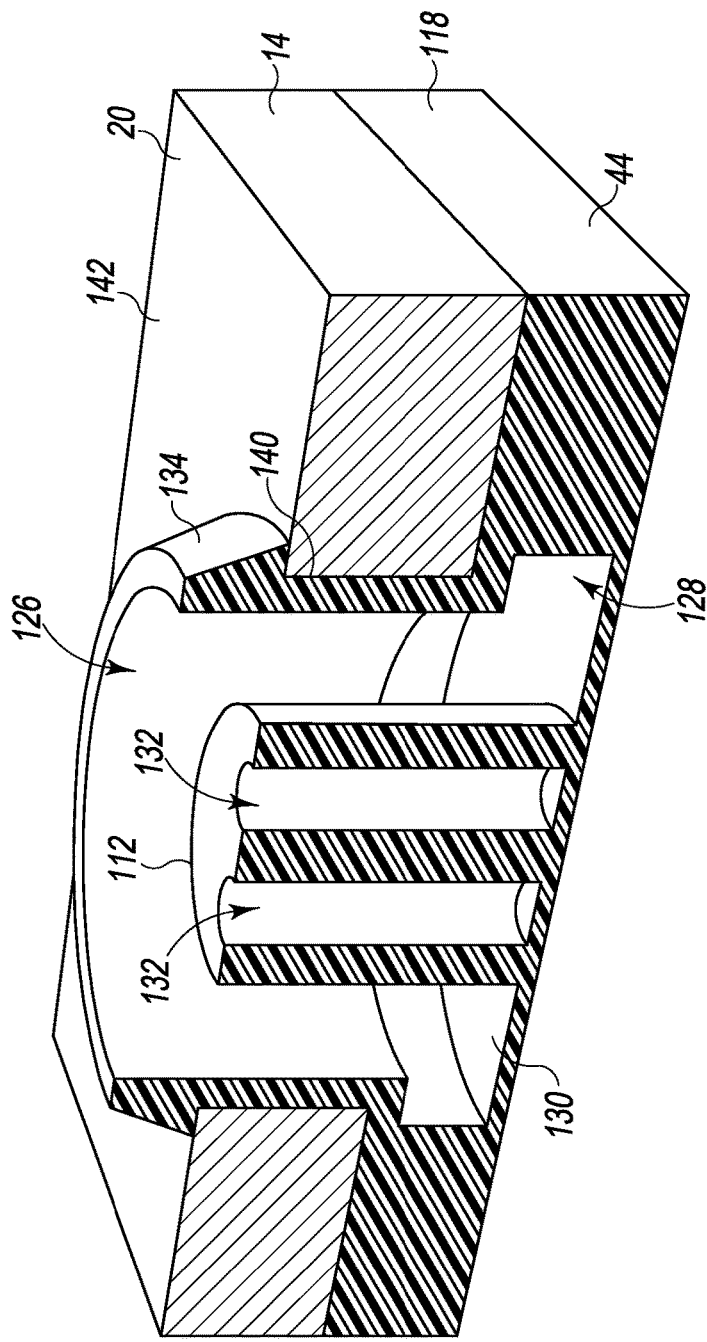
FIG. 8A is a cut-away view of the connector of the lower housing coupled to the surgical instrument case of FIG. 2.
Figure 8B:
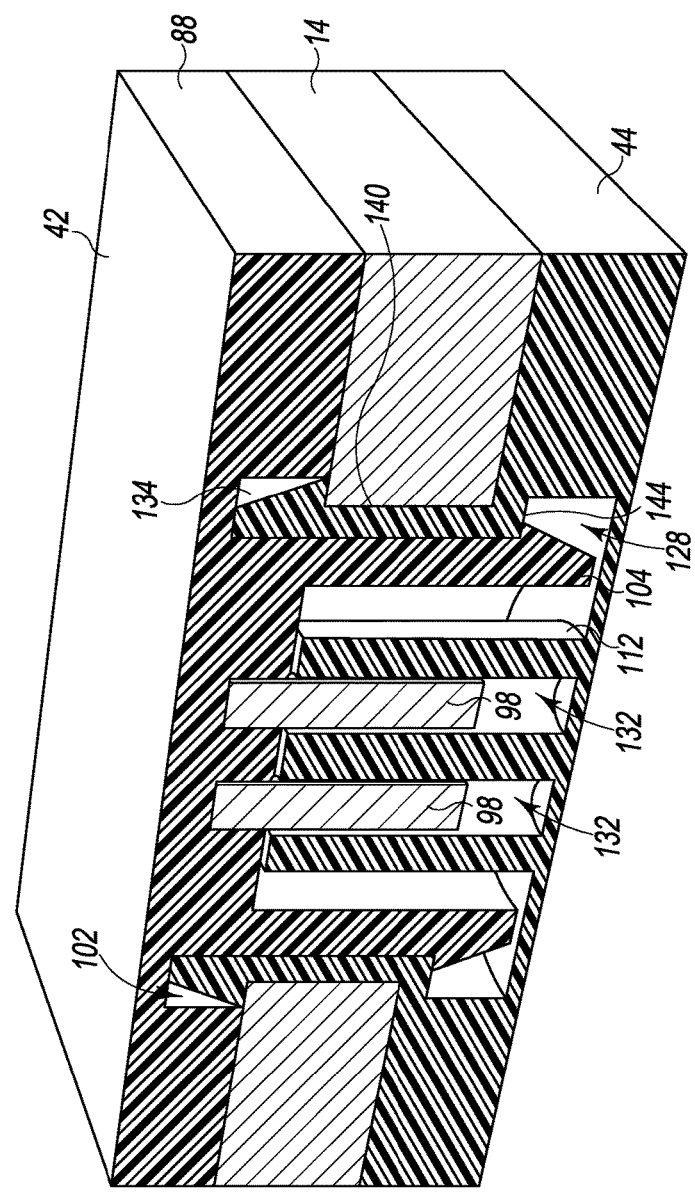
FIG. 8B is a cut-away view of the connector assembly of the surgical instrument case of FIG. 2.

The charging plate 40 may be attached to the bottom wall 20 of the instrument case 14 as shown in FIGS. 8A-8B. Referring now to FIG. 8A, the connector 110 of the lower housing 44 may be aligned with an opening 140 defined in the bottom wall 20. The distal end 120 of the connector 110 may be advanced through the opening 140. Because the connector body 114 is formed from a deformable plastic material, the flange 134 of the connector 110 may bend or flex to pass through the opening 140. When the flange 134 is through the opening 140, it resumes its undeformed shape and engages the upper surface 142 of the bottom wall 20. Because the flange 134 is larger in diameter than the opening 140, the connector 110 is retained in the opening 140, thereby securing the lower housing 44 to the bottom wall 20. It should be appreciated that in other embodiments the lower housing 44 may include additional pins, screws, or other fasteners to secure the lower housing 44 to the case 14.

Referring now to FIG. 8B, the upper housing connector 80 may be aligned with the aperture 126 of the lower housing connector 110 to assembly the connector assembly 50. The connector 80 may be advanced toward the lower housing connector 110 to deform flange 104 of the connector 80 and move it into the aperture 126. As the distal end 90 is advanced down the aperture 126, the prongs 98 of the plug 82 are advanced into the receptacles 132 of the socket 112. When the connector 80 is fully seated in the aperture 126 as shown in FIG. 8B, flange 104 resumes its undeformed shape and expands into the annular groove 128 defined at the base 130 of the aperture 126. The flange 104 engages the rim surface 144 of the connector 110, thereby securing the connector 80 to the connector 110. It should be appreciated that the connector assembly 50 may include an o-ring or other seal to provide a barrier between the electrical components and any external moisture.

Figure 9:
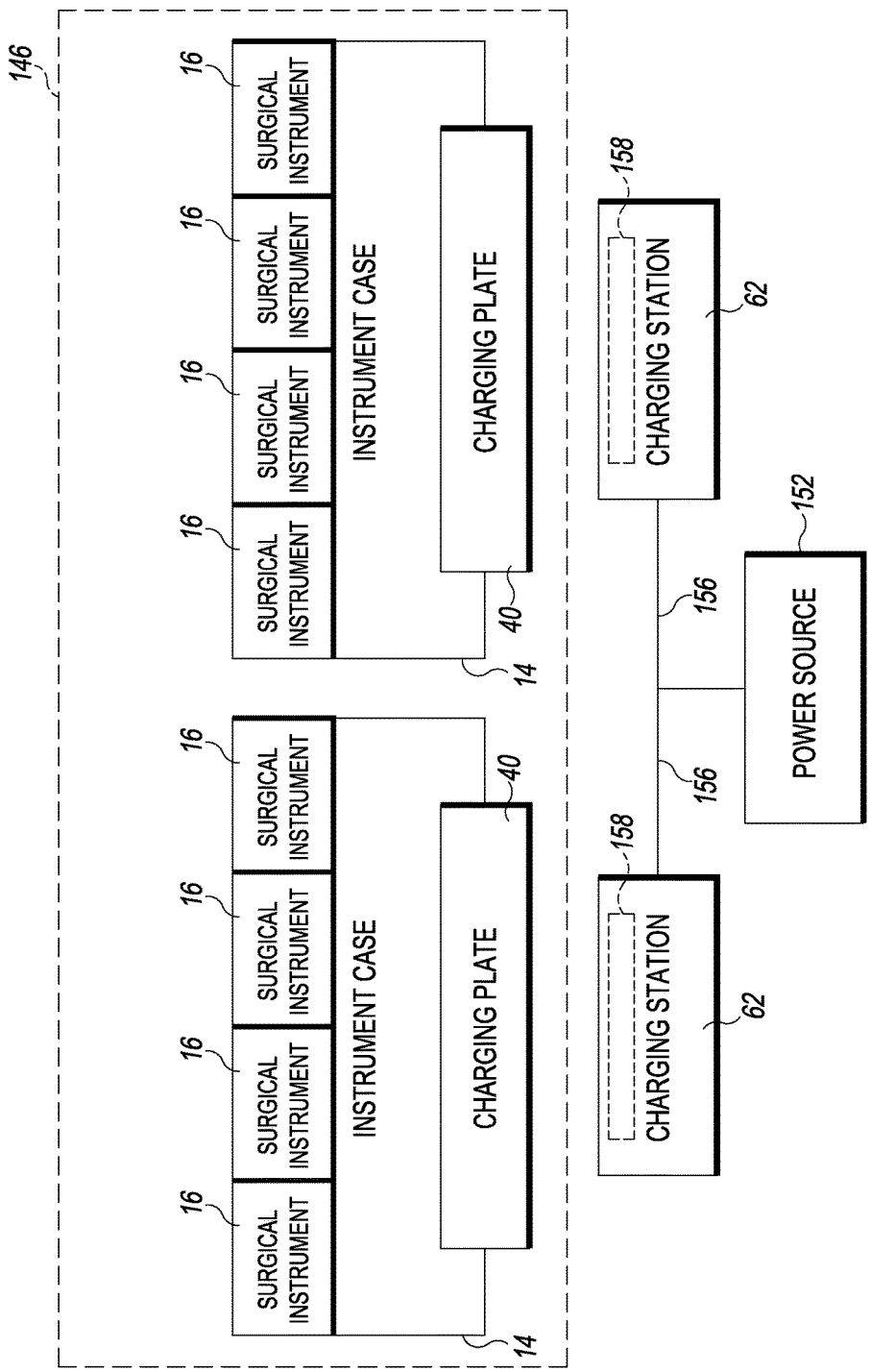
FIG. 9 is a block diagram of a surgical instrument system of FIG. 1.

In use, the surgical instrument system 10 for a particular surgical procedure may include more than one surgical instrument case 14 and more than one set of surgical instruments 12. As shown in FIG. 9, the instrument cases 14 and the instruments 12 are positioned in a sterile surgical field area 146 of an operating room for use in the surgical procedure. The system 10 includes a power source 152 connected to a charging station 62 for each case 14. The power source 152 and charging stations 62 are positioned outside of the sterile field area 146 under a surgical drape or behind another barrier that separates the sterilized operating theater from the unsterilized areas of the room or hospital. In an embodiment of the invention, the charging stations 62 may be positioned on the underside of a table used in an operating room.

The power source 152 is illustratively an AC power generator. It should be appreciated that in other embodiments the source 152 any number of power sources, including a standard wall plug or a battery, or a non-standard power source, whether AC or DC. The power source 152 provides power to the charging stations 62 through electrical cords 156. Each charging stations 62 include a primary coil 158 that is adapted to transmit power to one of the cases 14, as described in greater detail below. In other embodiments, the charging stations 62 may include internal power sources.

Figure 10:
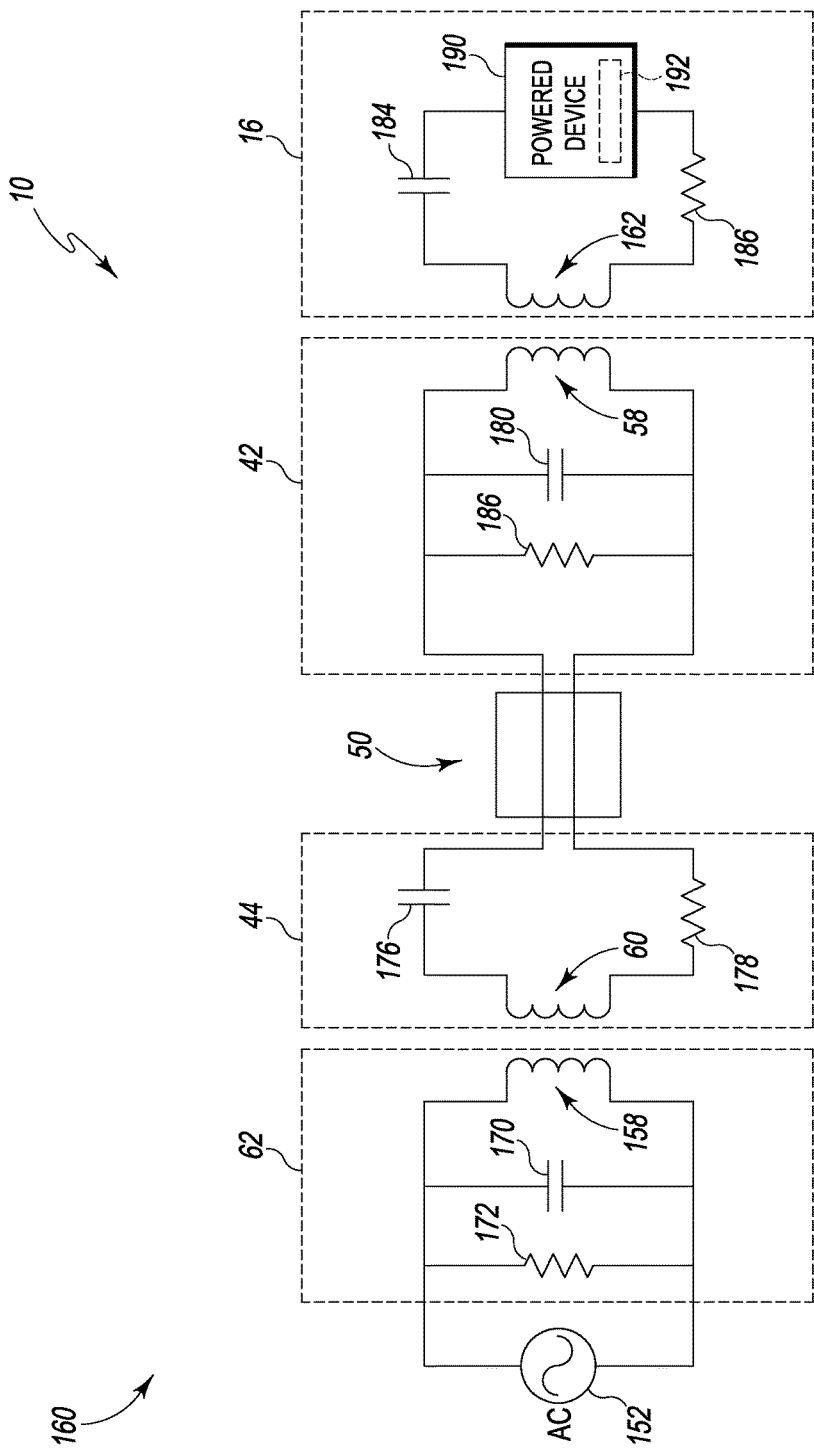
FIG. 10 is a circuit diagram of the surgical instrument system of FIG. 1.

Referring now to FIG. 10, the power circuit 160 of the system 10 is shown in greater detail. The power source 152 is configured to provide an alternating current power signal to the primary coil 158 of the charging station 62. In response to the power signal, the primary coil 158 generates an alternating magnetic field. When the case 14 is positioned near the charging station 62, the secondary coil 60 of the charging plate 40 is inductively coupled with the primary coil 158 of the charging station 62. Because the case 14 is formed from metal, the primary coil 58 is isolated from the primary coil 158 of the charging station 62. With the coils 60, 158 inductively coupled, the alternating magnetic field generated by primary coil 158 induces a current in the secondary coil 60, thereby transferring energy from the primary coil 158 to the secondary coil 60. The inducted alternating current may then be transferred to the primary coil 58 of the charging plate 40 via the connector assembly 50.

As shown in FIG. 10, each surgical instrument 16 includes a secondary coil 162, which is inductively coupled with the primary coil 58 of the charging plate 40 when the instrument 16 is placed in the chamber 18 of the case 14. In response to the inducted alternating current supplied by the secondary coil 60, the primary coil 58 of the charging plate 40 generates an alternating magnetic field, which induces a current in the secondary coil 162, thereby transferring energy from the primary coil 58 to the secondary coil 162. In that way, power may be supplied from outside the sterile field area 146 to an instrument 16 positioned in the surgical field area.

Each charging station 62 includes a tuning capacitor 170 and resister 172 coupled in parallel with the primary coil 158 (i.e., the capacitor 170, resister 172, and primary coil 158 form a parallel resonance circuit). It should be appreciated that in other embodiments the capacitor 170 and resister 172 may be arranged in series with the primary coil 158 and may include a resister or other tuning components. The tuning capacitor 170 and resister 172 are used to configure the resonant frequency of the primary coil 158. That is, the capacitance and resistance values of the tuning capacitor 170 and resister 172, respectively, are selected such that the resulting resonant frequency of the primary coil 158 matches the resonant frequency of the secondary coil 60 of the charging plate 40.

As shown in FIG. 10, the circuitry 66 of the charging plate 40 includes a capacitor 176 and a resistor 178 connected in series with the secondary coil 60 to tune the secondary coil 60 to match the resonant frequency of the charging station 62. That is, the capacitance value of the tuning capacitor 176 and the resistance value of resistor 178 are selected such that the resulting resonant frequency of the secondary coil 60 is equal to a predetermined frequency. Furthermore, the series nature of the electrical circuitry 66 provides for a higher bandwidth of frequencies that the power transfer can be accomplished. It should be appreciated that in other embodiments the capacitor 176 and the resistor 178 may be arranged in parallel with the secondary coil 60 and may include other tuning components. The resonant frequency of the coils 60, 158 may be in the range of 10 kHz to 125 kHz.

By matching the resonant frequencies of the coils 60, 158, the efficiency of the energy transfer between the coils 60, 158 is improved. As used herein in reference to resonant frequencies, the terms "match", "matched", and "matches" are intended to mean that the resonant frequencies are the same as or within a predetermined tolerance range of each other. For example, the resonant frequency of the primary coil 158 would match the resonant frequency of the secondary coil if the current induced in the secondary coil 60 is sufficient to power an electrical circuit or device coupled therewith. Conversely, the resonant frequencies of the coils 60, 158 would not match if the current induced in the secondary coil 60 is insufficient to power the primary coil 58 of the charging plate 40 and hence the surgical instruments 16.

As shown in FIG. 10, the charging plate 40 also includes a tuning capacitor 180 and resister 182 coupled in parallel with the primary coil 58 (i.e., the capacitor 180, resister 182, and primary coil 58 form a parallel resonance circuit). It should be appreciated that in other embodiments the capacitor 180 and resister 182 may be arranged in series with the primary coil 58 and may include a resister or other tuning components. The tuning capacitor 180 and resister 182 are used to configure the resonant frequency of the primary coil 58. That is, the capacitance and resistance values of the tuning capacitor 180 and resister 182, respectively, are selected such that the resulting resonant frequency of the primary coil 58 matches the resonant frequency of the secondary coil 162 of the surgical instrument 12.

The surgical instrument 12 also includes a capacitor 184 and a resistor 186 connected in series with the secondary coil 162 to tune the secondary coil 162 to match the resonant frequency of the primary coil 58 of the charging plate 40. That is, the capacitance value of the tuning capacitor 184 and the resistance value of the resistor 186 are selected such that the resulting resonant frequency of the secondary coil 162 is equal to a predetermined frequency. It should be appreciated that in other embodiments the capacitor 184 and the resistor 186 may be arranged in parallel with the secondary coil 162 and may include other tuning components. The resonant frequency of the coils 60, 158 may be in the range of 10 kHz to 125 kHz. Again, by matching the resonant frequencies of the coils 58, 162, the efficiency of the energy transfer between the coils 58, 162 is improved.

In some embodiments, the resonant frequencies of the primary coils 58, 158 may be adjustable to match the resonant frequencies of other secondary coils of other surgical or prosthetic devices. In this way, different devices (i.e. the secondary coils of the devices) may have different resonant frequencies to allow selective energy transfer to one device while reducing the amount of energy inadvertently transferred to other devices (i.e., the resonant frequencies of the other devices do not match the resonant frequencies of the primary coils 58, 158). The resonant frequencies of the primary coils may, however, be adjusted to match the resonant frequency of the other devices to transfer energy to such devices.

In addition, in some embodiments, the tuning capacitors 170, 180 and resisters 172, 182 may be selected such that the quality factor (Q) of the resulting resonance curve is high. In such embodiments, the resonant frequency of the primary coils 58, 158 matches a narrower bandwidth of frequencies. In addition, in some embodiments, the tuning capacitors 176, 184 and resistors 178, 186 are selected such that the quality factor (Q) of the resulting resonance curve is low. In such embodiments, the resonant frequency of the secondary coils 60, 162 matches a broader bandwidth of frequencies.

As shown in FIG. 10, each surgical instrument 16 includes an electrically-powered device 190. The device 190 may be embodied as any electrical circuit(s), electrical device(s), or combination thereof, capable of being housed in or on the instrument 16 and powered by the current produced by the secondary coil 162 or by an energy storage device 192. The energy storage device 192 may be embodied as any device capable of storing an amount of energy for later use by the instrument 16. For example, the energy storage device 192 may be embodied as a rechargeable battery such as a nickel cadmium battery or a storage capacitor and associated circuitry. Regardless, the energy storage device 192 is configured to be charged (i.e., energy is stored in the device 192) while the instrument 16 is being powered by the cooperation of the power circuit 160. Once the instrument 16 is no longer receiving power from the secondary coil 162, the energy storage device 192 begins providing power to the instrument 16. Once the energy storage device 192 becomes drained of energy, the instrument 16 may be recharged via the power circuit 160.

The surgical instrument 16 may include, but is not limited to, sensors such as magnetic sensors, load sensors, chemical sensors, biological sensors, and/or temperature sensors; processors or other circuits; electrical motors; actuators; and the like. In some embodiments, the powered device 190 may also include a transmitter (not shown) to transmit information using any suitable wireless communication protocol such as, for example, Bluetooth, wireless USB, Wi-Fi, WiMax, Zigbee, or the like.

Figure 11:
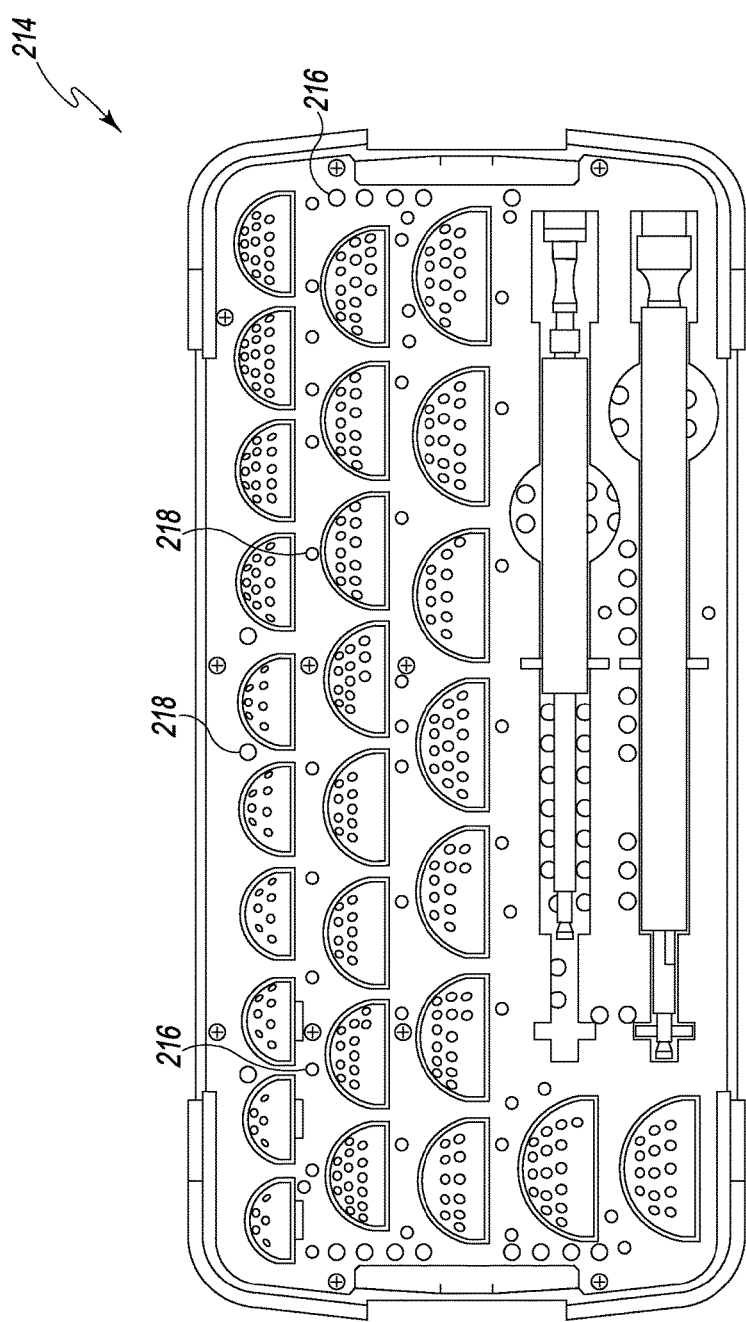
FIG. 11 is a top view of another embodiment of a surgical instrument system.

As shown in FIG. 11, a surgical instrument case 214 may also include a number of electrically-operated devices 216, such as, for example, light-emitting diodes (LEDs) 218, which may be operated by other circuitry to indicate when an instrument 16 is fully charged, indicate when an instrument is ready for use, or indicate which surgical instrument should be used next in a surgical procedure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A surgical instrument system, comprising:
 a plurality of surgical instruments configured for use during a surgical procedure,
 an instrument case including a bottom wall and a number of side walls extending upwardly from the bottom wall to define a chamber that receives the plurality of surgical instruments,
 a lower housing positioned outside of the chamber and removably coupled to the bottom wall of the metallic instrument case, the lower housing including a first induction coil, and
 an upper housing positioned in the chamber of the metallic instrument case, the upper housing including a second induction coil that is electrically connected to the first induction coil through one or more openings defined in the bottom wall of the metallic instrument case,
 wherein the plurality of surgical instruments includes a number of electrically-powered surgical instruments, each electrically-powered surgical instrument including a third inductive coil configured to receive power supplied inductively from the second induction coil.

2. The surgical instrument system of claim 1, wherein one of the lower housing and the upper housing includes a connector extending through an opening defined in the bottom wall of the metallic instrument case.

3. The surgical instrument system of claim 2, wherein:
the connector of one of the lower housing and the upper housing is a first connector, and
the other of the lower housing and the upper housing includes a second connector that is secured to an inner hub of the first connector.

4. The surgical instrument system of claim 3, wherein the lower housing includes the first connector, and the first connector includes a flange engaged with an upper surface of the bottom wall.

5. The surgical instrument system of claim 4, wherein:
the first connector and the second connector electrically connect the second induction coil to the first induction coil, and
the second induction coil is energized by the first induction coil through the electrical connection.

6. The surgical instrument system of claim 1, further comprising a primary induction coil configured to be positioned outside of a sterile environment, wherein the first induction coil is configured to be energized wirelessly by the primary induction coil.

7. The surgical instrument system of claim 1, wherein the lower housing includes a first circuit system.

8. The surgical instrument system of claim 1, wherein the upper housing includes a second circuit system.

9. The surgical instrument system of claim 1, wherein at least a portion of the instrument case is made of metal.

10. A method for providing power to a sterile environment, the method comprising:
positioning an instrument case assembly within the sterile environment, the instrument case assembly including a case defining an inner chamber, a lower housing secured to a lower surface of the case outside of the inner chamber and including a first induction coil, and an upper housing positioned in the inner chamber of the case and including a second induction coil electrically connected to the first induction coil,
positioning a primary induction coil outside of the sterile environment, and
energizing the primary induction coil to supply power to the second induction coil through the first induction coil,
wherein the second inductive coil inductively supplies power to at least one surgical instrument positioned in the chamber.

11. The method of claim 10, wherein the second induction coil is electrically connected to the first induction coil by a connector extending through the lower surface of the case.

12. The method of claim 11, wherein the upper housing is secured to a bottom wall of the case opposite the lower housing.

13. A surgical instrument system, comprising:
a plurality of surgical instruments configured for use during a surgical procedure,
an instrument case including a bottom wall and a number of side walls extending upwardly from the bottom wall to define a chamber that receives the plurality of surgical instruments,
a lower housing positioned outside of the chamber and secured to the bottom wall of the metallic instrument case, the lower housing including a first induction coil,
a primary induction coil configured to be positioned outside of a sterile environment, and
an upper housing positioned in the chamber of the metallic instrument case, the upper housing including a second induction coil that is electrically connected to the first induction coil through one or more openings defined in the bottom wall of the metallic instrument case,
wherein the plurality of surgical instruments includes a number of electrically-powered surgical instruments, each electrically-powered surgical instrument including a third inductive coil configured to receive power supplied inductively from the second induction coil, and
wherein the first induction coil is configured to be energized wirelessly by the primary induction coil.

14. The surgical instrument system of claim 13, wherein the lower housing includes a first circuit system.

15. The surgical instrument system of claim 13, wherein the upper housing includes a second circuit system.

16. The surgical instrument system of claim 13, wherein one of the lower housing and the upper housing includes a connector extending through an opening defined in the bottom wall of the metallic instrument case.

17. The surgical instrument system of claim 13, wherein:
the connector of one of the lower housing and the upper housing is a first connector, and
the other of the lower housing and the upper housing includes a second connector that is secured to an inner hub of the first connector.

18. The surgical instrument system of claim 17, wherein the lower housing includes the first connector, and the first connector includes a flange engaged with an upper surface of the bottom wall.

19. The surgical instrument system of claim 13, wherein at least a portion of the instrument case is made of metal.

* * * * *